United States Patent [19]

Yajima et al.

[11] Patent Number: 4,653,908
[45] Date of Patent: Mar. 31, 1987

[54] GRAZING INCIDENCE REFLECTION SPECTROMETER

[75] Inventors: Yusuke Yajima; Seiichi Murayama, both of Kokubunji; Kanji Tsujii, Nishitama, all of Japan

[73] Assignee: Hitachi, Ltd., Tokyo, Japan

[21] Appl. No.: 677,245

[22] Filed: Dec. 3, 1984

[30] Foreign Application Priority Data

Dec. 2, 1983 [JP] Japan ............................ 58-226856

[51] Int. Cl.4 ............................................. G01J 3/32
[52] U.S. Cl. ..................................... 356/51; 250/372; 356/327; 356/445
[58] Field of Search ......................... 356/51, 445–448, 356/369, 327, 322, 128, 364; 250/225, 372; 350/394–395

[56] References Cited

U.S. PATENT DOCUMENTS

| | | | |
|---|---|---|---|
| 3,765,773 | 10/1973 | Weiner | 356/364 |
| 3,880,524 | 4/1975 | Dill et al. | 356/369 |
| 4,077,720 | 3/1978 | Kasai | 356/369 |
| 4,264,209 | 4/1981 | Brewster | 356/51 X |
| 4,521,522 | 6/1985 | Lundstrom et al. | 356/364 X |

OTHER PUBLICATIONS

Sparrow et al., "Reflection Polarization by a Transparent-Film-Absorbing-Substrate System", vol. 62, No. 10, Oct. 1972, pp. 1188–1194, Journ. of Optical Society of America.
Kawamura et al., "Surface Structure Analysis by X-ray Spectroscopy & Diffraction" Jour. of the Spectroscopical Society of Japan, vol. 31, #4, 1982, pp. 269–281.
Süetaka, "Spectroscopies in Infrared Visible, & Near Ultraviolet Regions for the Investigation of Solid Surfaces" Jour. of the Spectroscopical Society of Japan, vol. 31, #3, 1982, pp. 195–210.

Primary Examiner—Vincent P. McGraw
Attorney, Agent, or Firm—Antonelli, Terry & Wands

[57] ABSTRACT

The present invention consists in a grazing incidence reflection spectrometer wherein light is caused to incide on a surface of a sample, and an intensity of light reflected from the sample surface is detected, thereby to measure an electronic absorption spectrum of a material adsorbed to the sample surface, characterized in that the incident light is visible light or ultraviolet light, and that the incident light has a predetermined glancing angle to the sample surface.

4 Claims, 8 Drawing Figures

GRAZING INCIDENCE REFLECTION SPECTROMETER

BACKGROUND OF THE INVENTION

The present invention relates to a grazing incidence reflection spectrometer which operates to direct light obliquely onto a sample surface and detects the light which is reflected therefrom, whereby the electronic absorption spectrum of a chemical species at the sample surface is measured with a high sensitivity.

With the development of fine dry processing in the production of a semiconductor device etc., it is required to exactly determine a reaction mechanism at a solid-gas interface. Therefore, several studies have been made on methods and apparatuses for non-destructively observing an adsorption phenomenon which is the initial process of the surface reaction.

Among them, a method of measurement with the traveling direction of incident light set at an angle at which it is nearly parallel to a sample surface has already been employed for total reflection and Bragg reflection measurements in the X-ray region as stated in, for example, an article by T. Kawamura and T. Fukamachi ('Journal of the Spectroscopical Society of Japan', Vol. 31, No. 4, 1982, pp. 269–281). According to this method, it is possible to obtain information on a crystal structure in the vicinity of the sample surface and the structure and the nature of bonding of a layered adsorption film at the sample surface. With such measurement method, however, it is difficult to obtain detailed knowledge on the electronic structure of a chemical species which is adsorbed to the sample surface in a non-layered fashion.

Here, unless otherwise specified, the "sample" shall indicate a substrate which includes a smooth surface having no chemical species adsorbed thereto, and the "chemical species adsorbed to the sample surface" shall signify a chemical species which has an interaction with the sample surface including ordinary physical adsorption or chemical adsorption (the same applies hereinbelow).

In addition, a measurement method wherein linearly polarized light whose plane containing the electric vector and the direction of propagation (referred to as the "plane of polarization" henceforth) is parallel to a plane of incidence is used as incident light and an angle defined between the incident light and the sample surface is set at about 20° to 30° so as to enlarge the amplitude of electric field vibration at the sample surface, has been employed for the reflection spectrometry of the adsorbed molecular species of a metallic sample surface in the infrared region (by W. Suëtaka in 'Journal of the Spectroscopical Society of Japan', Vol. 31, No. 3, 1982, pp. 195–210). According to this measurement method, knowledge on the nature of the bonding between the adsorbed molecular species and the sample is obtained from the vibrational spectrum of the adsorbed molecular species. With only this measurement method, however, it is difficult to obtain detailed information on the electronic structure as concerns the mechanism of the surface reaction of the sample. Moreover, this measurement method is restricted to the case where the sample is metal, and it is also subject to the limit in application that the adsorbed species must be a molecule.

SUMMARY OF THE INVENTION

It is accordingly an object of the present invention to provide a grazing incidence reflection spectrometer which can measure an electronic absorption spectrum based on a chemical species adsorbed to a sample surface, at sufficient sensitivity without being appreciably affected by the transmission of incident light through a sample or the decay thereof in the sample.

In order to accomplish the object, according to the present invention, a grazing incidence reflection spectrometer wherein light is caused to be incident on a surface of a sample, and the intensity of light reflected from the sample surface is detected, thereby to measure an electronic absorption spectrum of a material adsorbed to the sample surface, is so constructed that the incident light is visible light or ultraviolet light, and that said incident light has a predetermined glancing angle to the sample surface.

Owing to such characterizing construction of the present invention, the electronic absorption spectrum of a chemical species adsorbed to the sample surface can be measured at high sensitivity. Moreover, the sample is not restricted to an opaque material, but it may be a transparent material as well. Besides, whether the adsorbed chemical species is a molecule or an atom, the electronic absorption spectrum is permitted to be measured at high sensitivity.

DETAILED DESCRIPTION

First, the principle of the present invention will be explained.

The mechanism by which light in the visible and ultraviolet regions is absorbed into a material can be understood as a process in which an electron within the material undergoes transition to a higher energy state owing to the energy of the light. Accordingly, the absorption spectrum of the light in the visible and ultraviolet regions is called the "electronic absorption spectrum".

It has been revealed from various experiments and studies that the electronic absorption spectrum of a chemical species adsorbed to the surface of a sample can be obtained by causing the light of the visible and ultraviolet regions to be incident on the surface of the sample and by measuring the intensity of light reflected from the sample surface. It has also been acknowledged that, whether the chemical species adsorbed to the sample surface is an atom or a molecule in this case, the electronic absorption spectrum thereof can be measured. However, the electronic absorption spectrum mentioned above has the drawback of a very low measurement sensitivity though it has been acknowledged to be, in principle, measurable. More specifically, in a case where the sample is an opaque material such as a semiconductor or metal, a conventional method of absorption measurement in which the intensity ratio of transmitted light to incident light is measured does not apply to the measurement of the electronic absorption spectrum of the visible light or ultraviolet light for the chemical species adsorbed to the sample surface, because a sufficient intensity of the transmitted light is not attained due to the absorption in the sample. Also in a case where a transparent material such as glass is the sample, the total number of the adsorbed chemical species distributed in two dimensions is slight in an optical path, and hence, the application of the conventional method of absorption measurement is difficult in point of the detection sensitivity.

The drawback is therefore solved by defining a glancing angle so that the reflectivity of the incident light from the sample may come sufficiently close to 1 (one), and then measuring the electronic absorption spectrum on the basis of the reflected light.

Upon further experiments and studies, it has been revealed that conditions to be described below may be set in order to enhance the detection sensitivity.

Figure 1:
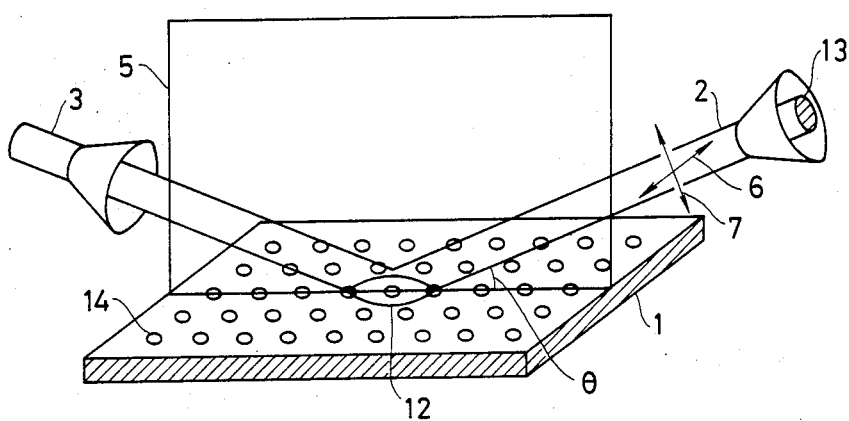
FIG. 1 is a principle arrangement view for explaining the principle of the present invention.
Figure 2:
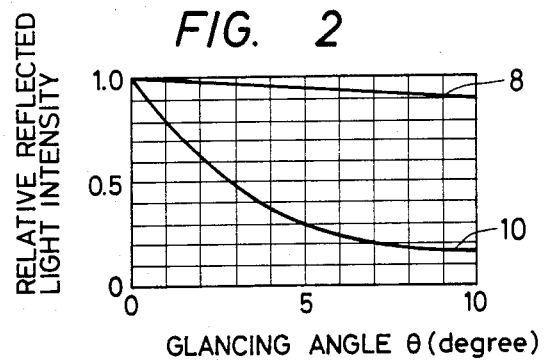
FIGS. 2 and 3 are graphs showing examples of the calculated results of the relationship between the relative reflected light intensity and the glancing angle in FIG. 1.
Figure 3:
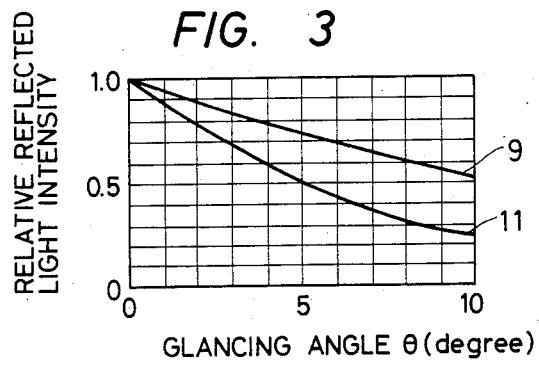

The conditions will be explained in conjunction with the principle arrangement of the spectrometer according to the present invention as illustrated in FIG. 1. The intensity of reflected light 3 relative to the intensity of light 2 entering a flat sample 1 whose surface has no chemical species adsorbed thereto, depends upon the real part and imaginary part of the complex refractive index of the sample 1, an angle $\theta$ defined between the sample 1 and the incident light 2, and the direction of polarization of the incident light 2 with respect to a plane 5 containing the incident light 2 and the reflected light 3. Hereinbelow, the angle $\theta$ shall be termed the "glancing angle $\theta$", and the plane 5 the "plane of incidence 5". Shown in FIGS. 2 and 3 are examples of results obtained by calculating the dependence of the relative reflected light intensity on the glancing angle $\theta$ as to a case where the incident light 2 in a direction 6 perpendicular to the plane of incidence 5 and a case where it is polarized in a direction 7 parallel thereto. In FIG. 2, the real part of a complex refractive index is set at 3.46, and the imaginary part at 3.25. Besides, in FIG. 3, the real part of a complex refractive index is set at 1.52, and the imaginary part at 0. The complex refractive index in the case of FIG. 2 corresponds substantially to the value of tungsten for the visible light, and that in the case of FIG. 3 to the value of glass. A curve 8 in FIG. 2 and a curve 9 in FIG. 3 are of the case where the incident light 2 in FIG. 1 is polarized in the direction 6 perpendicular to the plane of incidence 5. A curve 10 in FIG. 2 and a curve 11 in FIG. 3 are of the case where the incident light 2 in FIG. 1 is polarized in the direction 7 parallel to the plane of incidence 5. As seen from FIGS. 2 and 3, when the incident light 2 in FIG. 1 polarized in the direction 6 perpendicular to the plane of incidence 5 is used, relative reflected light intensities close to 1 (one) can be attained over an extensive range of glancing angles $\theta$. In order to actually verify this, experiments were conducted on the samples 1 of various materials. As a result, it has been found that, for the sample 1 of an opaque material such as a semiconductor or metal, when the glancing angle $\theta$ is set within 5°, 90% or more of the incident light 2 is reflected from the sample 1, so the loss of the light attributed to the sample 1 itself is negligible in practical use. In addition, in a case where the glancing angle $\theta$ falls within the above range, the area of the light irradiation part 12 of the sample 1 in FIG. 1 becomes at least 10 times as large as the area of the cross section 13 of the incident light 2. Further, in a case where the material of the sample 1 is a transparent material such as glass, a situation similar to the above is realized by setting the glancing angle $\theta$ within 1°. This was quite true even when the incident light 2 was the ultraviolet light. Under such condition, the relative reflected light intensities were recorded while the wavelength of the incident light 2 was being changed. Then, it has been acknowledged that the electronic absorption spectrum of a chemical species 14 adsorbed to a large area on the sample 1 can be measured at a sufficient sensitivity without being affected by the loss of the light ascribable to the sample 1.

Figure 4:
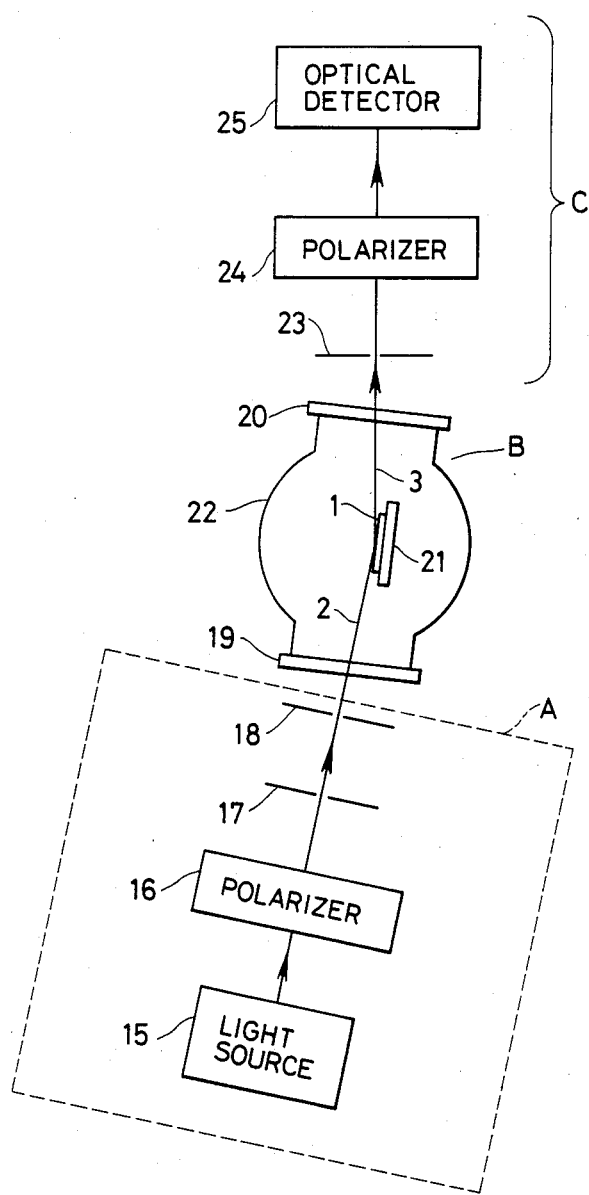
FIG. 4 is a block diagram showing the fundamental arrangement of an embodiment of a grazing incidence reflection spectrometer according to the present invention.
Figure 5:
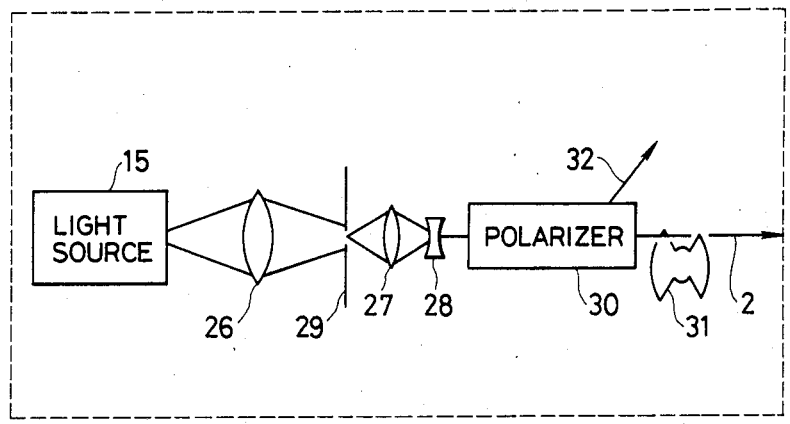
FIG. 5 is an arrangement diagram showing another embodiment of an incident light supply section in the present invention.
Figure 6:
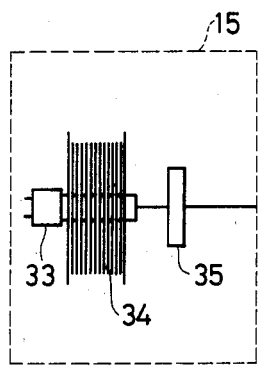
FIGS. 6, 7 and 8 are setup diagrams each showing an embodiment of a light source in the present invention.
Figure 7:
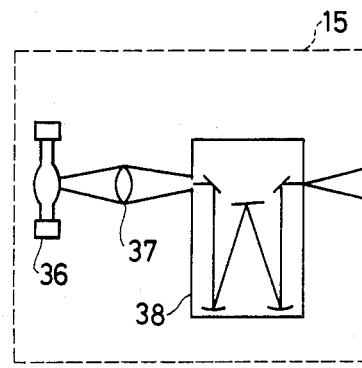
Figure 8:
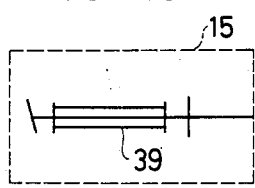

Next, a practicable embodiment of the grazing incidence reflection spectrometer according to the present invention will be described with reference to the drawings. FIG. 4 shows the fundamental arrangement of the spectrometer according to the present invention. An incident light supply section A is constructed of a light source 15 capable of varying visible and ultraviolet wavelengths in a wavelength range of about 200 nm to about 700 nm, a polarizer 16, and pinholes 17, 18. A sample section B is made up of a vacuum chamber 22 which comprises optical windows 19, 20 of quartz at both its ends, and a sample support 21 for holding a sample 1. A reflected light detection section C is constructed of a pinhole 23, a polarizer 24 and an optical detector 25. The glancing angle $\theta$ of incident light 2 relative to the sample 1 is set so as to fulfill the condition mentioned before. The incident light 2 emergent from the incident light supply section A passes through the quartz window 19 and irradiates the sample 1 in the vacuum chamber 22, whereupon light 3 reflected from the sample is received by the optical detector 25 via the quartz window 20 as well as the polarizer 24. With the incident light supply section A in FIG. 4, only that linearly polarized component of light from the light source 15 whose plane of polarization is perpendicular to the plane of incidence is derived by the polarizer 16, and it is put into a collimated beam by the pinholes 17, 18. Another embodiment of the incident light supply section A is shown in FIG. 5. With this incident light supply section A which is constructed of a light source 15, lenses 26, 27, 28, a pinhole 29, a polarizer 30 and an optical chopper 31, light emitted from the light source 15 is focused on the pinhole 29 by the lens 26 and is put into a collimated beam by the lenses 27, 28. The collimated beam is led to the polarizer 30 so as to split polarization components. On component 32 of the polarization components is used for the reference of an incident light intensity, while the other is used as incident light 2 on the sample 1. The incident light 2 is chopped by the optical chopper 31, and the phase sensitive detection is employed, thereby to enhance the detection sensitivity. FIGS. 6, 7 and 8 show practicable embodiments of the light source 15. In FIG. 6, the light source 15 is composed of a hollow cathode lamp 33, an electromagnet 34 and a quarter wave plate 35. With this light source 15 which exploits the Zeeman effect on an atomic level within a magnetic field, the hollow cathode lamp 33 is inserted in the electromagnet 34, and current to flow through the electromagnet 34 is changed, whereby the wavelength of the line spectrum of an atom is changed by the effect. In a case where the magnetic field is applied in parallel with an optical axis as illustrated in FIG. 6, the light given forth is, in general, circularly polarized light, and hence, a linearly polarized light is obtained through the quarter wave plate. It is needless to say that the magnetic field can also be applied perpendicularly to the optical axis. With such setup, it is possible to find the profile of the electronic absorption spectrum of a chemical species adsorbed to the surface of the sample, and to obtain information on the electronic structure. In FIG. 7, the light source 15 is composed of a xenon arc lamp 36, a lens 37 and a spectrometer 38. Continuous light emitted from the xenon arc lamp 36 is focused on the slit of the spectrometer 38 by the lens 37 so as to obtain monochromatic light. In FIG. 8, the light source 15 is composed of a dye laser of variable wavelengths or an excimer laser of variable wavelengths 39.

According to the apparatus thus far described, even when the adsorbed chemical species had a surface density of $10^{13}/cm^2$ or so, namely, an average distance of 30 Å or so, the electronic absorption spectrum thereof could be obtained with a sufficient sensitivity.

In this manner, according to the present invention, the electronic absorption spectrum of the visible or ultraviolet region for a chemical species adsorbed to the surface of a sample can be measured at a sufficient sensitivity without being hampered by the loss in the sample.

When the electronic absorption spectrum of the adsorbed chemical species as obtained by utilizing the present invention is compared with an electronic absorption spectrum in the case where the same chemical species exists freely, detailed knowledge on the change of the electronic structure to be incurred by the adsorption is obtained from the difference of the spectra.

Such information serves as an important key for understanding, for example, the initial process of a surface reaction, which forms the basis of semiconductor dry processing technology, and it is indispensable to developing a higher degree of processing technology.

The present invention is also characterized in that the sample surface is not irradiated with a particle beam such as electron beam or ion beam, and that electron emission, ion emission etc. from the sample surface are not involved, either. Accordingly, when compared with a photoelectron spectrometer or a surface measurement instrument employing an electron beam or ion beam, the present invention is excellent in that the surface state is disturbed little.

What is claimed is:

1. A grazing incidence reflection spectrometer comprising:
    vacuum chamber means having first and second optical windows and providing a holder therein for holding in a vacuum a sample adsorbed chemical species having a surface to be measured;
    incident light supply means for directing onto said surface of said sample through said first optical window an incident light which varies in wavelength in the range of 200 nm to 700 nm and has a glancing angle with respect to the surface of said sample such that the reflectivity from said sample of the incident light not absorbed by the sample comes close to one; and
    reflected light detection means for detecting the light which is reflected from the surface of said sample and which passes through said second optical window in order to measure the electronic absorption spectrum of said chemical species adsorbed on the surface of said sample by observing a variation of the intensity of the light reflected from the surface of said sample for wavelengths within said range.

2. A grazing incidence reflection spectrometer according to claim 1, wherein said incident light is linearly polarized light whose plane of polarization is perpendicular to a plane of incidence.

3. A grazing incidence reflection spectrometer according to claim 2, wherein the sample is made of an opaque material, and said glancing angle does not exceed 5°.

4. A grazing incidence reflection spectrometer according to claim 2, wherein the sample is made of a transparent material, and said glancing angle does not exceed 1°.

* * * * *